United States Patent
Bartos et al.

(10) Patent No.: US 10,414,712 B2
(45) Date of Patent: Sep. 17, 2019

(54) PURIFIED TEREPHTHALIC ACID (PTA) VENT STEAM UTILIZATION

(71) Applicant: BP Corporation North America Inc., Houston, TX (US)

(72) Inventors: Thomas Bartos, Arden, NC (US); Kathryn Buckalew, Chicago, IL (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 15/823,951

(22) Filed: Nov. 28, 2017

(65) Prior Publication Data

US 2018/0186719 A1 Jul. 5, 2018

Related U.S. Application Data

(60) Provisional application No. 62/440,217, filed on Dec. 29, 2016.

(51) Int. Cl.
*C07C 51/43* (2006.01)
*B01D 3/34* (2006.01)
(Continued)

(52) U.S. Cl.
CPC .............. *C07C 51/43* (2013.01); *B01D 3/343* (2013.01); *B01D 53/70* (2013.01); *B01D 53/76* (2013.01); *B01D 53/86* (2013.01); *C07C 51/16* (2013.01); *C07C 51/265* (2013.01); *C07C 51/42* (2013.01); *C07C 63/26* (2013.01); *B01J 2219/00006* (2013.01); *C07C 51/255* (2013.01);
(Continued)

(58) Field of Classification Search
CPC ......... C07C 51/16; C07C 51/36; C07C 51/42; C07C 51/43; C07C 51/255; C07C 51/265; C07C 63/14; C07C 63/15; C07C 63/26; C07C 51/487; B01D 3/343
See application file for complete search history.

(56) References Cited

U.S. PATENT DOCUMENTS 2,741,369 A 5/1953 Fest
5,723,656 A 3/1998 Abrams
(Continued)

FOREIGN PATENT DOCUMENTS

| EP | 0 962 442 | 12/1999 |
|----|-----------|---------|
| WO | 2006/102459 | 9/2006 |
| WO | 2015/102655 | 7/2015 |

*Primary Examiner* — Yate' K Cutliff
(74) *Attorney, Agent, or Firm* — McDonnell Boehnen Hulbert & Berghoff LLP

(57) ABSTRACT

Processes for manufacturing a purified aromatic carboxylic acid include oxidizing a substituted aromatic compound in a reaction zone to form a crude aromatic carboxylic acid and a gaseous stream; heating the crude aromatic carboxylic acid in a pre-heating zone, contacting the crude aromatic carboxylic acid with hydrogen in the presence of a catalyst in a hydrogenation reactor to form a purified aromatic carboxylic acid, crystallizing the purified aromatic carboxylic acid in a crystallization zone to form a slurry stream comprising solid purified aromatic carboxylic acid and a vapor stream. At least a portion of the vapor stream is directed to the pre-heating zone and at least a portion of the vapor stream from the pre-heating zone is vented to the off-gas treatment zone in order to achieve energy savings.

10 Claims, 2 Drawing Sheets

(51) Int. Cl.
- *B01D 53/70* (2006.01)
- *B01D 53/76* (2006.01)
- *B01D 53/86* (2006.01)
- *C07C 51/16* (2006.01)
- *C07C 63/26* (2006.01)
- *C07C 51/265* (2006.01)
- *C07C 51/42* (2006.01)
- C07C 51/487 (2006.01)
- C07C 51/36 (2006.01)
- C07C 51/255 (2006.01)

(52) U.S. Cl.
CPC ............ *C07C 51/36* (2013.01); *C07C 51/487* (2013.01); *Y02P 20/131* (2015.11)

(56) References Cited

U.S. PATENT DOCUMENTS

| | | | |
|---|---|---|---|
| 6,137,001 A | 10/2000 | Brooker et al. | |
| 7,807,060 B2 | 10/2010 | Schmid | |
| 7,935,844 B2 * | 5/2011 | Bartos | B01D 3/009 |
| | | | 562/408 |
| 8,173,834 B2 | 5/2012 | Bartos | |
| 2005/0051473 A1 | 3/2005 | Suss et al. | |
| 2012/0006745 A1 | 1/2012 | Kaley et al. | |
| 2012/0142962 A1 | 6/2012 | Ure | |
| 2015/0183709 A1 * | 7/2015 | Bartos | C07C 51/42 |
| | | | 562/416 |

\* cited by examiner

PURIFIED TEREPHTHALIC ACID (PTA) VENT STEAM UTILIZATION

TECHNICAL FIELD

The present teachings relate generally to processes for manufacturing aromatic carboxylic acids, and in particular, to processes for purifying crude aromatic carboxylic acids.

BACKGROUND

Terephthalic acid (TA) and other aromatic carboxylic acids may be used in the manufacture of polyesters (e.g., via their reaction with ethylene glycol and/or higher alkylene glycols). Polyesters in turn may be used to make fibers, films, containers, bottles, other packaging materials, molded articles, and the like.

In commercial practice, aromatic carboxylic acids have been made by liquid phase oxidation of methyl-substituted benzene and naphthalene feedstocks in an aqueous acetic acid solvent. The positions of the methyl substituents correspond to the positions of carboxyl groups in the aromatic carboxylic acid product. Air or other sources of oxygen (e.g., typically in a gaseous state) have been used as oxidants in the presence, for example, of a bromine-promoted catalyst that contains cobalt and manganese. The oxidation is exothermic and yields aromatic carboxylic acid together with by-products, including partial or intermediate oxidation products of the aromatic feedstock, and acetic acid reaction products (e.g., methanol, methyl acetate, and methyl bromide). Water is also generated as a by-product.

Pure forms of aromatic carboxylic acids are oftentimes desirable for the manufacture of polyesters to be used in important applications (e.g., fibers and bottles). Impurities in the acids (e.g., by-products generated from oxidation of aromatic feedstocks and, more generally, various carbonyl-substituted aromatic species) are thought to cause and/or correlate with color formation in polyesters made therefrom, which in turn leads to off-color in polyester converted products. Aromatic carboxylic acids having reduced levels of impurities may be made by further oxidizing crude products from liquid phase oxidation as described above at one or more progressively lower temperatures and oxygen levels. In addition, partial oxidation products may be recovered during crystallization and converted into the desired acid product.

Pure forms of terephthalic acid and other aromatic carboxylic acids having reduced amounts of impurities—for example, purified terephthalic acid (PTA)—have been made by catalytically hydrogenating less pure forms of the acids or so-called medium purity products in solution using a noble metal catalyst. In commercial practice, liquid phase oxidation of alkyl aromatic feed materials to crude aromatic carboxylic acid, and purification of the crude product, are oftentimes conducted in continuous integrated processes in which crude product from the liquid phase oxidation is used as a starting material for the purification.

In order for the hydrogenation to proceed at a satisfactory rate, it is necessary to use excess hydrogen, which is expensive. This hydrogen goes into the vapor phase in the first PTA crystallizer. The vapor from the PTA first crystallizer is used to preheat the slurry going into the PTA hydrogenation reactor to save energy. The vapor enters the shell side of the exchanger. In conventional purification units, due to the presence of non-condensable hydrogen, it is necessary to vent a small fraction of the steam/hydrogen from the exchanger resulting in a loss of hydrogen and heat value. The hydrogen can be recovered and recycled as taught in the art, but this requires additional capital in the form of equipment and still requires a small purge to prevent impurity buildup.

There continues to be a need to reduce the overall costs of manufacturing aromatic carboxylic acids.

SUMMARY

The scope of the present invention is defined solely by the appended claims, and is not affected to any degree by the statements within this summary.

According to one aspect of the invention, a process for manufacturing a purified aromatic carboxylic acid is provided. The process comprises oxidizing a substituted aromatic compound in a reaction zone to form a crude aromatic carboxylic acid and a gaseous stream; heating the crude aromatic carboxylic acid in a pre-heating zone; contacting the crude aromatic carboxylic acid with hydrogen in the presence of a catalyst in a hydrogenation reactor to form a purified aromatic carboxylic acid; crystallizing the purified aromatic carboxylic acid in a crystallization zone to form a slurry stream comprising solid purified aromatic carboxylic acid and a vapor stream, wherein the vapor stream comprises steam and hydrogen; recovering a purified carboxylic acid product from the slurry; directing at least a portion of the vapor stream to the pre-heating zone in order to heat the crude aromatic carboxylic acid; venting at least a portion of the vapor stream from the pre-heating zone to an off-gas treatment zone, the off-gas treatment zone configured to treat at least of portion of the gaseous stream formed by the oxidization of the substituted aromatic compound; and recovering energy from the vapor stream in the off-gas treatment zone.

According to another aspect of the invention, an apparatus for manufacturing a purified aromatic carboxylic acid is provided. The apparatus comprises a reaction zone configured for oxidizing a substituted aromatic compound to form a crude carboxylic acid and a gaseous stream; a pre-heating zone configured for heating the crude carboxylic acid; a hydrogenation reactor configured for contacting the crude aromatic carboxylic acid with hydrogen in the presence of a catalyst to form a purified aromatic carboxylic acid; a crystallization zone configured for crystallizing the purified aromatic carboxylic acid to form a slurry stream comprising solid purified aromatic carboxylic acid and a vapor stream, wherein the vapor stream comprises steam and hydrogen; a recovery zone configured for recovering a purified carboxylic acid product from the slurry; and an off-gas treatment zone configured to treat at least a portion of the gaseous stream formed by oxidization of the substituted aromatic compound, wherein at least a portion of the vapor stream is directed to the pre-heating zone in order to heat the crude aromatic carboxylic acid, wherein at least a portion of the vapor stream from the pre-heating zone is vented to the off-gas treatment zone, and wherein energy from the vapor stream is recovered in the off-gas treatment zone.

Other aspects of the invention will be apparent to those skilled in the art in view of the description that follows.

DETAILED DESCRIPTION

Figure 1A:
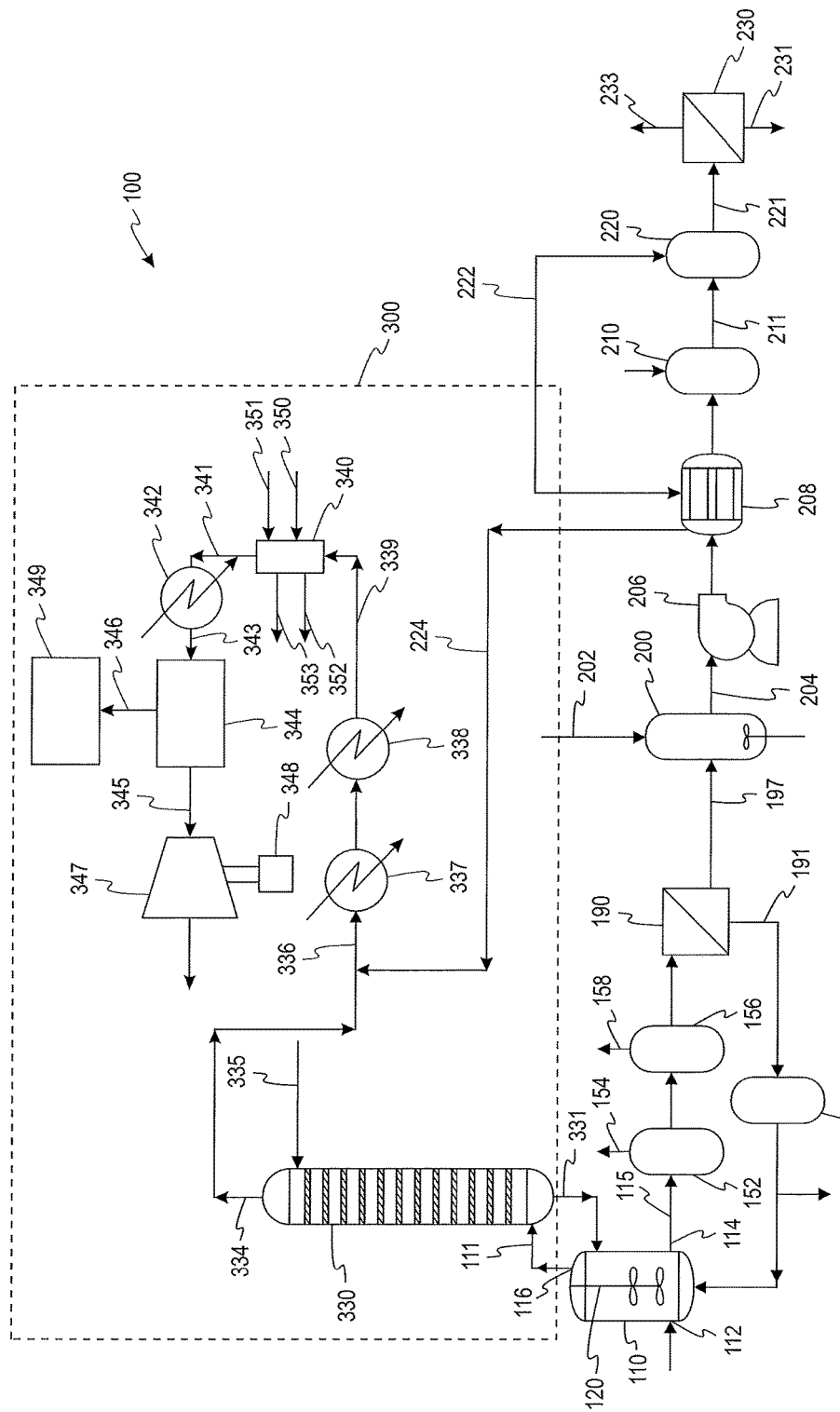
FIGS. 1A and 1B show a process flow diagram for manufacturing purified forms of aromatic carboxylic acids in accordance with the present teachings.

By way of general introduction, a process for manufacturing a purified aromatic carboxylic acid in accordance with the present invention comprises: oxidizing a substituted aromatic compound in a reaction zone to form a crude aromatic carboxylic acid and a gaseous stream; heating the crude aromatic carboxylic acid in a pre-heating zone; contacting the crude aromatic carboxylic acid with hydrogen in the presence of a catalyst in a hydrogenation reactor to form a purified aromatic carboxylic acid; crystallizing the purified aromatic carboxylic acid in a crystallization zone to form a slurry stream comprising solid purified aromatic carboxylic acid and a vapor stream, wherein the vapor stream comprises steam and hydrogen; recovering a purified carboxylic acid product from the slurry; directing at least a portion of the vapor stream to the pre-heating zone in order to heat the crude aromatic carboxylic acid; venting at least a portion of the vapor stream from the pre-heating zone to an off-gas treatment zone, the off-gas treatment zone configured to treat at least of portion of the gaseous stream formed by the oxidization of the substituted aromatic compound; and recovering energy from the vapor stream in the off-gas treatment zone. In some embodiments, the pre-heating zone comprises a heat exchanger and the vapor stream enters a shell side of the heat exchanger. In some embodiments, the off-gas treatment zone comprises at least one heat exchanger, a catalytic oxidation unit, and an expander.

In some embodiments, the process further comprises distilling the gaseous stream in a distillation column to form a distilled gaseous stream. In some embodiments, the at least a portion of the vapor stream may be vented upstream of the at least one heat exchanger. In some embodiments, the at least a portion of the vapor stream is vented to a stream leading to the catalytic oxidation unit in order to heat the distilled gaseous stream.

In some embodiments, the process further comprises directing the distilled gaseous stream to the catalytic oxidation unit, wherein the distilled gaseous stream comprises methyl bromide; burning hydrogen in the vapor stream in the catalytic oxidation unit; oxidizing methyl bromide in the catalytic oxidation unit to form bromine; forming a first catalytic oxidation effluent and a second catalytic oxidation effluent; and directing the first catalytic oxidation effluent to the expander, wherein the expander recovers energy from the first catalytic oxidation effluent. In some embodiments, the process further comprises directing the second catalytic oxidation effluent to a scrubber; and removing bromine from the second catalytic oxidation effluent with the scrubber. In some embodiments, the temperature of the first catalytic oxidation effluent entering the expander is greater than 150 degrees Celsius.

An apparatus for manufacturing a purified aromatic carboxylic acid in accordance with the present invention comprises: a reaction zone configured for oxidizing a substituted aromatic compound to form a crude carboxylic acid and a gaseous stream; a pre-heating zone configured for heating the crude carboxylic acid; a hydrogenation reactor configured for contacting the crude aromatic carboxylic acid with hydrogen in the presence of a catalyst to form a purified aromatic carboxylic acid; a crystallization zone configured for crystallizing the purified aromatic carboxylic acid to form a slurry stream comprising solid purified aromatic carboxylic acid and a vapor stream, wherein the vapor stream comprises steam and hydrogen; a recovery zone configured for recovering a purified carboxylic acid product from the slurry; and an off-gas treatment zone configured to treat at least a portion of the gaseous stream formed by oxidization of the substituted aromatic compound, wherein at least a portion of the vapor stream is directed to the pre-heating zone in order to heat the crude aromatic carboxylic acid. In some embodiments, at least a portion of the vapor stream from the pre-heating zone is vented to the off-gas treatment zone. In some embodiments, energy from the vapor stream is recovered in the off-gas treatment zone.

In some embodiments, the apparatus further comprises a distillation column configured for distilling the gaseous stream to form a distilled gaseous stream. In some embodiments, the catalytic oxidation unit is configured to oxidize the distilled gaseous stream to form a catalytic oxidation effluent. In some embodiments, the expander is configured to recover energy from the catalytic oxidation effluent.

Additional features of the above-described processes for manufacturing purified forms of aromatic carboxylic acid in accordance with the present teachings will now be described in reference to the drawing figures.

Figure 1B:
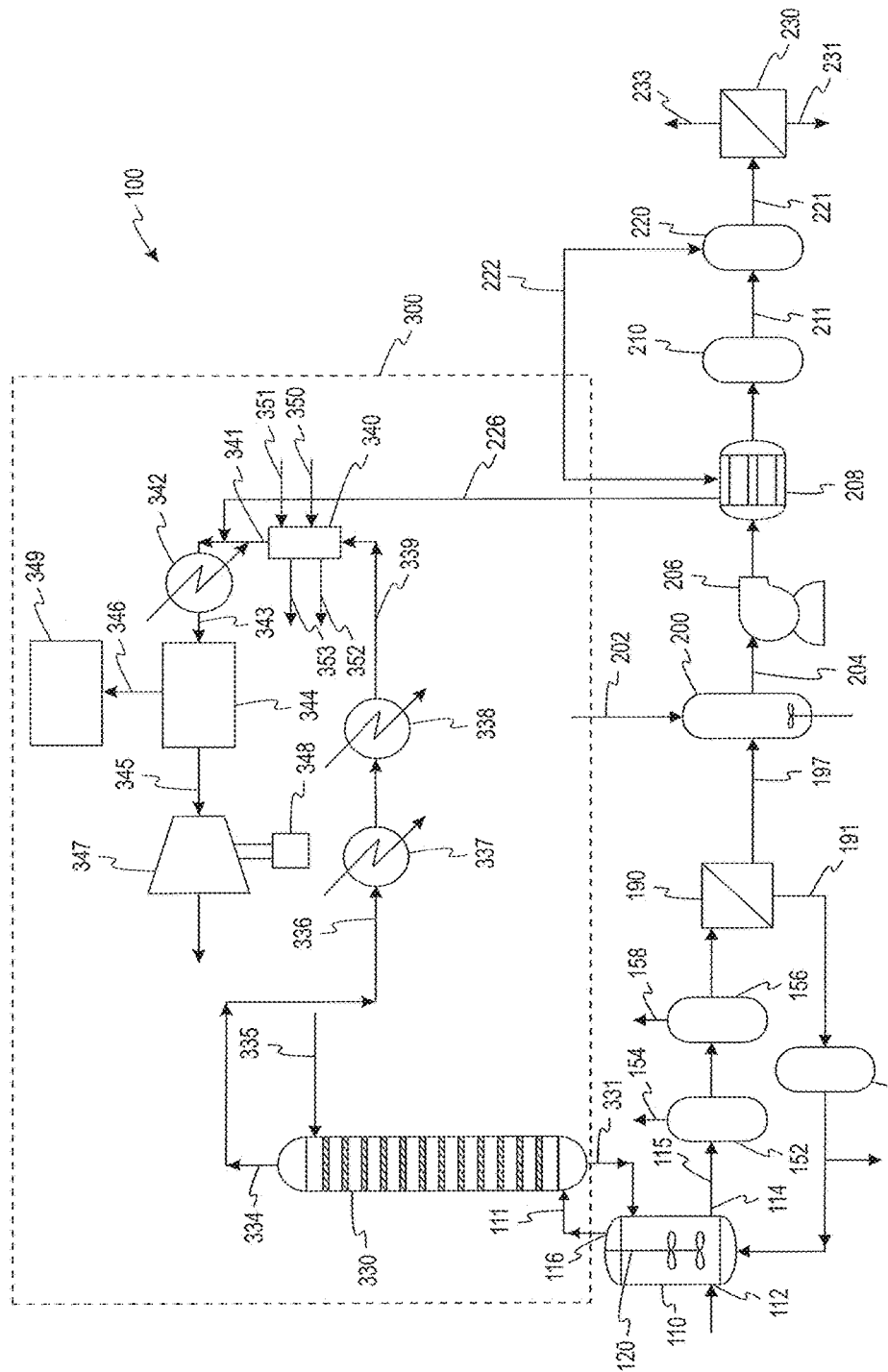

FIGS. 1A and 1B show a process flow diagram for manufacturing purified forms of aromatic carboxylic acids in accordance with one embodiment of the present invention. As a brief introduction, the process 100 includes a reaction zone comprising an oxidation reactor 110 configured for liquid phase oxidation of feedstock; a crystallization zone configured for forming crude aromatic carboxylic acid from the liquid phase oxidation reaction mixture, and comprising crystallization vessels 152 and 156; a solid-liquid separation device 190 configured for separating crude aromatic carboxylic acid (and some oxidation by-products and intermediaries) from liquid, a mixing zone including a purification reaction mixture make up vessel 200 configured for preparing mixtures of crude aromatic carboxylic acid in purification reaction solvent; a pre-heating zone including a heat exchanger 208 for heating the crude aromatic carboxylic acid prior to its introduction into a purification zone, a purification zone including a hydrogenation reactor 210 configured for contacting the crude aromatic carboxylic acid with hydrogen in the presence of a catalyst to form a purified aromatic carboxylic acid; and a recovery zone comprising a crystallization zone including vessel 220 configured for forming a slurry stream comprising solid purified aromatic carboxylic acid and a vapor stream, wherein the vapor stream comprises steam and hydrogen; and a solid-liquid separation device 230 configured for separating purified solid product from liquid.

The integration of processes in FIGS. 1A and 1B is meant to be purely representative, and various other integrated, and non-integrated configurations may likewise be used.

Liquid and gaseous streams and materials used in the process represented in FIGS. 1A and 1B may be directed and transferred through suitable transfer lines, conduits, and piping constructed, for example, from materials appropriate for process use and safety. It will be understood that particular elements may be physically juxtaposed and, where appropriate, may have flexible regions, rigid regions, or a combination of both. In directing streams or compounds, intervening apparatuses and/or optional treatments may be included. By way of example, pumps, valves, manifolds, gas and liquid flow meters and distributors, sampling and sensing devices, and other equipment (e.g., for monitoring, controlling, adjusting, and/or diverting pressures, flows and other operating parameters) may be present.

Representative aromatic feedstock materials suitable for use in the oxidation reactor 110 include but are not limited to aromatic compounds (e.g., hydrocarbons) substituted at one or more positions with at least one group that is oxidizable to a carboxylic acid group. In some embodiments, the positions of the substituents correspond to the positions of the carboxylic acid groups of the aromatic carboxylic acid being prepared. In some embodiments, the oxidizable substituents include alkyl groups (e.g., methyl, ethyl, and/or isopropyl groups). In other embodiments, the oxidizable substituents include oxygen-containing groups, such as a hydroxyalkyl, formyl, aldehyde, and/or keto groups. The substituents may be the same or different. The aromatic portion of feedstock compounds may be a benzene nucleus or it may be bi- or polycyclic (e.g., a naphthalene and/or anthracene nucleus). In some embodiments, the number of oxidizable substituents on the aromatic portion of the feedstock compound is equal to the number of sites available on the aromatic portion. In other embodiments, the number of oxidizable substituents on the aromatic portion of the feedstock is fewer than all such sites (e.g., in some embodiments 1 to 4 and, in some embodiments, 2). Representative feed compounds that may be used in accordance with the present teachings—alone or in combinations—include but are not limited to toluene; ethylbenzene and other alkyl-substituted benzenes; o-xylene; p-xylene; m-xylene; tolualdehydes, toluic acids, alkyl benzyl alcohols, 1-formyl-4-methylbenzene, 1-hydroxymethyl-4-methylbenzene; methylacetophenone; 1,2,4-trimethylbenzene, 1-formyl-2,4-dimethyl-benzene; 1,2,4,5-tetramethyl-benzene; alkyl-, formyl-, acyl-, and hydroxylmethyl-substituted naphthalenes (e.g., 2,6-dimethylnaphthalene, 2,6-diethylnaphthalene, 2,7-dimethylnaphthalene, 2,7-diethylnaphthalene, 2-formyl-6-methylnaphthalene, 2-acyl-6-methylnaphthalene, 2-methyl-6-ethylnaphthalene, and the like); and the like; and partially oxidized derivatives of any of the foregoing; and combinations thereof. In some embodiments, the substituted aromatic compound comprises a methyl-, ethyl-, and/or isopropyl-substituted aromatic hydrocarbon. In some embodiments, the substituted aromatic compound comprises an alkyl-substituted benzene, o-xylene, p-xylene, m-xylene, or the like, or combinations thereof.

Aromatic carboxylic acids manufactured in accordance with the present teachings are not restricted and include but are not limited to mono- and polycarboxylated species having one or more aromatic rings. In some embodiments, the aromatic carboxylic acids are manufactured by reaction of gaseous and liquid reactants in a liquid phase system. In some embodiments, the aromatic carboxylic acid comprises only one aromatic ring. In other embodiments, the aromatic carboxylic acid comprises a plurality (e.g., two or more) aromatic rings that, in some embodiments, are fused (e.g., naphthalene, anthracene, etc.) and, in other embodiments, are not. In some embodiments, the aromatic carboxylic acid comprises only one carboxylic acid (e.g., —CO$_2$H) moiety or a salt thereof (e.g., —CO$_2$X, where X is a cationic species including but not limited to metal cations, ammonium ions, and the like). In other embodiments, the aromatic carboxylic acid comprises a plurality (e.g., two or more) of carboxylic acid moieties or salts thereof. Representative aromatic carboxylic acids include but are not limited to terephthalic acid, trimesic acid, trimellitic acid, phthalic acid, isophthalic acid, benzoic acid, naphthalene dicarboxylic acids, and the like, and combinations thereof. In some embodiments, the present teachings are directed to manufacture of pure forms of terephthalic acid including purified terephthalic acid (PTA) and so-called medium purity terephthalic acids.

A representative type of oxidation that may be conducted in the oxidation reactor 110 is a liquid phase oxidation that comprises contacting oxygen gas and a feed material comprising an aromatic hydrocarbon having substituents oxidizable to carboxylic acid groups in a liquid phase reaction mixture. In some embodiments, the liquid phase reaction mixture comprises a monocarboxylic acid solvent and water in the presence of a catalyst composition comprising at least one heavy metal component (e.g., Co, Mn, V, Mo, Cr, Fe, Ni, Zi, Ce, Hf, or the like, and combinations thereof) and a promoter (e.g., halogen compounds, etc.). In some embodiments, the oxidation is conducted at elevated temperature and pressure effective to maintain a liquid phase reaction mixture and form a high temperature, high-pressure vapor phase. In some embodiments, oxidation of the aromatic feed material in the liquid phase oxidation produces aromatic carboxylic acid as well as reaction by-products, such as partial or intermediate oxidation products of the aromatic feed material and/or solvent by-products. In some embodiments, the aromatic carboxylic acid comprises terephthalic acid, and the oxidizing comprises contacting para-xylene with gaseous oxygen in a liquid phase oxidation reaction mixture that comprises acetic acid, water, and a bromine-promoted catalyst composition. The liquid-phase oxidation and associated processes may be conducted as a batch process, a continuous process, or a semi-continuous process. The oxidation may be conducted in one or more reactors.

In a representative embodiment, such as may be implemented as shown in FIGS. 1A and 1B, liquid feed material comprising at least about 99 wt. % substituted aromatic hydrocarbon, aqueous acetic acid solution (e.g., containing about 70 to about 95 wt. % acetic acid), soluble compounds of cobalt and manganese (e.g., such as their respective acetates) as sources of catalyst metals, bromine (e.g., hydrogen bromide) as catalyst promoter, and air may be continuously charged to oxidation reaction vessel 110 through inlets, such as inlet 112. In some embodiments, vessel 110 is a pressure-rated, continuous-stirred tank reactor.

In some embodiments, stirring may be provided by rotation of an agitator 120, the shaft of which is driven by an external power source (not shown). Impellers mounted on the shaft and located within the liquid body are configured to provide forces for mixing liquids and dispersing gases within the liquid body, thereby avoiding settling of solids in the lower regions of the liquid body.

In some embodiments, para-xylene is oxidized in reactor 110, predominantly to terephthalic acid. By-products that may form in addition to terephthalic acid include but are not limited to partial and intermediate oxidation products (e.g., 4-carboxybenzaldehyde, 1,4-hydroxymethyl benzoic acid, p-toluic acid, benzoic acid, and the like, and combinations thereof). Since the oxidation reaction is exothermic, heat generated by the reaction may cause boiling of the liquid phase reaction mixture and formation of an overhead gaseous stream that comprises vaporized acetic acid, water vapor, gaseous by-products from the oxidation reaction, carbon oxides, nitrogen from the air charged to the reaction, unreacted oxygen, and the like, and combinations thereof.

In some embodiments, liquid effluent comprising solid oxidation products slurried in the liquid phase reaction mixture is removed from reaction vessel 110 through slurry outlet 114 and directed in stream 115 to crystallization vessel 152, and in turn crystallization vessel 156, for recovery of a solid product.

In some embodiments, solid crude product may be recovered from the liquid by crystallization in one or more stages, such as in a single crystallization vessel or, as shown in FIGS. 1A and 1B, in a series of multiple stirred crystallization vessels. In some embodiments, the crystallization process comprises sequential reductions in temperature and pressure from earlier to later stages to increase product recovery. By way of example, as shown in FIGS. 1A and 1B, crystallization vessels 152 and 156 may be provided in series and in fluid communication, such that product slurry from vessel 152 may be transferred to vessel 156. Cooling in the crystallization vessels may be accomplished by pressure release. One or more of the crystallization vessels may be vented, as at vents 154 and 158, to remove vapor resulting from pressure let down and generation of steam from the flashed vapor to a heat exchange means (not shown).

As shown in FIGS. 1A and 1B, the crystallization vessel 156 is in fluid communication with a solid-liquid separation device 190. The solid-liquid separation device 190 is configured to receive a slurry of solid product from the crystallization vessel 156. In some embodiments, the solid-liquid separation device 190 is further configured to separate a crude solid product and by-products from the liquid. In some embodiments, the separation device 190 is a centrifuge, a rotary vacuum filter, a pressure filter, or the like, or a combination thereof. In some embodiments, the separation device 190 comprises a pressure filter configured for solvent exchange (e.g., by positive displacement under pressure of mother liquor in a filter cake with wash liquid comprising water). Suitable rotary pressure filters are sold by BHS-Sonthofen and are disclosed for example, in U.S. Pat. Nos. 2,741,369 and 7,807,060, and United States Patent Application Publication No. 2005/0051473. The oxidation mother liquor resulting from the separation may exit separation device 190 in stream 191 for transfer to mother liquor drum 192. A portion of the mother liquor and, in some embodiments, a major portion of the mother liquor, may be transferred from drum 192 to oxidation reactor 110. In such a way, monocarboxylic acid solvent, water, catalyst, and/or oxidation reaction by-products dissolved and/or present as fine solid particles in the mother liquor may be returned to the liquid phase oxidation reaction.

As shown in FIGS. 1A and 1B, the stream 197 comprising heated crude solid product may be directed to a mixing zone including a reaction mixture make up vessel 200. The crude solid product in stream 197 may be mixed and slurried in make-up vessel 200 in with a make-up solvent entering vessel 200 through line 202 to form a purification reaction mixture comprising crude aromatic carboxylic acid. The purification reaction mixture prepared in vessel 200 is withdrawn through line 204 and transferred to pump 206. In some embodiments, the purification make-up solvent contains water. In some embodiments, the solvent line 202 connects to a holding vessel (not shown) for containing make-up solvent. In other embodiments, the solvent comprises fresh demineralized water fed from a deaerator. In other embodiments, the solvent is supplied from another part of the integrated process 100. For example, in one embodiment, the solvent comprises the condensate obtained from an off-gas separation in column 330 or from vapors recovered from a crystallization zone Sources of purification make-up solvent are more fully described, for example, in U.S. Pat. Nos. 5,723,656, 6,137,001, 7,935,844, 7,935,845, and 8,173,834. Suitable sources of purification make-up solvent include demineralized water, steam condensate, condensate from distillation in the oxidation section, such as overhead condensed from stream 334, and condensate from purification crystallizers such as 220.

Purification reaction mixture exiting vessel 200 through line 204 enters a pre-heating zone. The purification reaction mixture comprising the crude aromatic carboxylic acid is introduced into the pre-heating zone. The pre-heating zone shown in FIGS. 1A and 1B includes a pump 206 and a heat exchanger 208. Those skilled in the art will appreciate that although only one heat exchanger is shown in FIGS. 1A and 1B, the pre-heating zone may include additional heat exchangers configured in series or parallel. The heat exchanger 208 raises the temperature of the purification reaction mixture to a temperature required for a purification reaction using a supported catalyst.

The heated purification reaction mixture exits the pre-heating zone and enters the purification zone. The purification zone includes a purification reactor 210. In some embodiments, the purification reactor 210 is a hydrogenation reactor and purification in the purification reactor 210 comprises contacting the purification reaction mixture comprising crude aromatic carboxylic acid with hydrogen in the presence of a hydrogenation catalyst. In some embodiments, a portion of the purification liquid reaction mixture may be continuously removed from hydrogenation reactor 210 in stream 211 and directed to a crystallization vessel 220 in a downstream crystallization zone. In some embodiments, in crystallization vessel 220, terephthalic acid and reduced levels of impurities may be crystallized from the reaction mixture. The resulting slurry stream comprising solid purified aromatic carboxylic acid and liquid formed in vessel 220 may be directed to solid-liquid separation device 230 in stream 221. A resulting vapor stream comprising steam and hydrogen is directed to the heat exchanger 208 of the pre-heating zone in stream 222 in order to heat the crude carboxylic acid. In some embodiments, the vapor stream in stream 222 enters a shell side of the heat exchanger 208. Purified carboxylic acid product exits solid-liquid separation device 230 in the stream 231. In some embodiments, at least a portion, in some embodiments all or substantially all, of a purification mother liquor may be directed in stream 233 as reflux to high-pressure distillation column 330, as more fully described, for example, in U.S. Pat. Nos. 5,723,656, 6,137,001, 7,935,844, 7,935,845, and 8,173,834. In other embodiments, stream 233 may be directed to a waste water treatment facility. Yet another alternative is to cool the stream 233 for recovery of solid product as described in United States Patent Publication No. 2012/142962. The solid-liquid separation device 230 may be a centrifuge, a rotary vacuum filter, a pressure filter, or the like, or a combination thereof.

The process 100 further includes an off-gas treatment zone 300 configured to treat at least a portion of the gaseous stream formed by oxidization of the substituted aromatic compound. The off-gas treatment zone 300 comprises a distillation column 330, heat exchangers 337 and 338, a catalytic oxidation unit 344, and an expander 347. In some embodiments, at least a portion of the vapor stream from the heat exchanger 208 is vented to the off-gas treatment zone 300 in stream 224 or stream 226.

The gaseous stream may be removed from the reactor through vent 116 and sent in a stream 111 to the distillation column 330. The separation zone is configured to separate water from the solvent monocarboxylic acid and return a solvent-rich liquid phase to the reactor in line 331. A distilled gaseous stream is removed from the separation zone in line 334 and for further processed. In some embodiments, the distilled gaseous stream comprises nitrogen, oxygen, water, acetic acid, carbon oxides, and methyl bromide. Reflux is returned to the column 330 in line 335. The reflux fluid may include condensed portions of the water rich gas stream 334 or may include fluid from other sources. Examples of further processing of the overhead gas stream and sources of reflux fluids are more fully described in U.S. Pat. Nos. 5,723,656, 6,137,001, 7,935,844, 7,935,845, and 8,173,834.

In some embodiments, the at least a portion of the vapor stream is vented upstream of the heat exchangers 337 and 338 in stream 224 and combined with the distilled gaseous stream in stream 336, as shown in FIG. 1A. The vapor stream in stream 224 comprises steam and hydrogen. Energy is recovered from the steam in heat exchangers 337 and 338 by heating of a shell side fluid (not shown) and the stream 336 is cooled. The shell side fluid, such as water or another process stream, may be used to generate energy, for example, by generating steam for uses elsewhere in the process or by heating up the water or process stream for use at a later point. It is beneficial to add steam of stream 224 at this point in the process because energy can be recovered from the steam with the heat exchangers and because this portion of the process does not need to be kept dry. Uncondensed gas is then directed to a high pressure absorber 340 configured for removal of volatile components in stream 339. The volatile components can be removed by contacting the vapor with liquid, first with an acetic acid rich stream 350 and then with a water rich stream 351. The resulting scrubbing liquors 352 and 353 may be directed to other parts of the process, such as to the oxidation reactor 110.

Scrubbed vapor effluent from the high pressure absorber 340 is directed through stream 341 to a heat exchanger 342 configured to heat the vapor effluent to a temperature of about 120° C. The heated effluent is directed through stream 343 to the catalytic oxidation unit 344. The catalytic oxidation unit 344 comprises catalytic oxidation reactor (not shown) and a secondary heat exchanger (not shown) which recovers heat from a catalytic oxidation reactor effluent to raise the temperature of the stream entering the catalytic oxidation unit 344 to about 300° C. Hydrogen from the vapor stream (the at least a portion of the vapor stream that is vented in stream 224 upstream of the heat exchangers 337 and 338) is burned in the catalytic oxidation unit 344 which also results in recovery of energy. The catalytic oxidation unit 344 needs to be hot enough to destroy volatile organic compounds and to produce an effluent that is hot enough to avoid downstream corrosion problems (i.e., to keep the downstream process dry). Burning hydrogen from the at least a portion of the vapor stream increases the exothermic reaction heat generated by the catalytic oxidation unit 344, which allows for less energy input into the system which also results in a more economical process than conventional processes because excess fuel does not need to be added to the catalytic oxidation unit 344.

In some embodiments, the at least a portion of the vapor stream is vented to a stream 341 leading to the catalytic oxidation unit 344 in stream 226, as shown in FIG. 1B. The vapor stream in stream 226 comprises steam and hydrogen. Energy is recovered because the steam in the vapor stream heats stream 341 such that not as much additional energy is required to heat up stream 341 before entering the catalytic oxidation unit 344. However, liquid water is detrimental to the catalytic oxidation unit 344 and the downstream process. Thus, the temperature of stream 341 entering the catalytic oxidation unit 344 may need to be higher in order to vaporize the water. In addition, or alternatively, the temperature of the stream in the expander cannot be reduced by as much when the pressured is lowered (compared to the embodiment shown in FIG. 1A). Thus, less energy may be recovered by the expander. As in the process in FIG. 1A, hydrogen from the vapor stream (the at least a portion of the vapor stream that is vented in stream 226) is burned in the catalytic oxidation unit 344 which also results in recovery of energy. Burning hydrogen from the at least a portion of the vapor stream increases the exothermic reaction heat generated by the catalytic oxidation unit 344, which allows for less energy input into the system which also results in a more economical process than conventional processes because excess fuel does not need to be added to the catalytic oxidation unit 344.

Methyl bromide is oxidized in the catalytic oxidation unit 344 to form bromine and HBr. In some embodiments, a first catalytic oxidation effluent and a second catalytic oxidation effluent are formed. The first catalytic oxidation effluent is directed to the expander 347 via stream 345 and energy is recovered from the first catalytic oxidation effluent in a generator 348. In some embodiments, the second catalytic oxidation effluent is directed to a scrubber 349 in stream 346 for removal of bromine from the second catalytic oxidation effluent.

In some embodiments, the temperature of the first catalytic oxidation effluent entering the expander 347 in stream 345 is at greater than 150° C. In one embodiment, the temperature is greater than 170° C. The temperature of the first catalytic oxidation effluent in stream 345 is controlled by both the inlet temperature of the stream 343 entering the catalytic oxidation unit 344 and the heat of reaction across the catalytic oxidation reactor. Burning hydrogen from stream 224 or stream 226 increases the heat of reaction.

The entire contents of each and every patent and non-patent publication cited herein are hereby incorporated by reference, except that in the event of any inconsistent disclosure or definition from the present specification, the disclosure or definition herein shall be deemed to prevail.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

EXAMPLE

The following example is based on a computer simulation. The top row shows the benefit of adding hydrogen into the catalytic oxidation ("CATOX") system by venting the vapor stream from the pre-heating zone in the purification process. The CATOX effluent is typically routed to an expander. The hotter the inlet, the more energy can be recovered. Alternatively, less fuel or steam is needed to heat up the gas entering the CATOX reactor. Both result in energy savings. As shown in the table below, venting the vapor stream from the pre-heating zone allows for an increase in the temperature of the CATOX effluent entering the expander and thus for a more economical process than conventional processes.

It is necessary to maintain a certain temperature (>300° C.) in the CATOX system to ensure proper destruction of volatile organic compounds, such as methyl bromide. The hydrogen concentration in the overhead system is well below the lower explosion limit of 4% in air and thus does not constitute a safety risk.

PTA Purification Preheater Vents

| | With PTA preheat Hydrogen | W/O Hydrogen | Units | Δ kWh/ton PTA |
|---|---|---|---|---|
| Temperature into Expander | 174.3 | 168.4 | °C. | 1 |
| Additional Steam Generated | 0.02 | 0 | ton/ton PTA | 2 |
| Emission Reduction | | | | Reduction |
| Stack Methyl Bromide Test 1 | 7.5 | 13 | mg/nm3 | 42.3% |
| Stack Methyl Bromide Test 2 | 5 | 8 | mg/nm3 | 37.5% |

An approximately 40% reduction in concentration of methyl bromide from the overall process stack is observed for this process. Thus, emissions of methyl bromide are reduced compared to conventional processes.

The invention claimed is:

1. A process for manufacturing a purified aromatic carboxylic acid comprising:
   oxidizing a substituted aromatic compound in a reaction zone to form a crude aromatic carboxylic acid and a gaseous stream;
   heating the crude aromatic carboxylic acid in a pre-heating zone;
   contacting the crude aromatic carboxylic acid with hydrogen in the presence of a catalyst in a hydrogenation reactor to form a purified aromatic carboxylic acid;
   crystallizing the purified aromatic carboxylic acid in a crystallization zone to form a slurry stream comprising solid purified aromatic carboxylic acid and a vapor stream, wherein the vapor stream comprises steam and hydrogen;
   recovering a purified carboxylic acid product from the slurry;
   directing at least a portion of the vapor stream to the pre-heating zone in order to heat the crude aromatic carboxylic acid;
   venting at least a portion of the vapor stream from the pre-heating zone to an off-gas treatment zone, the off-gas treatment zone configured to treat at least a portion of the gaseous stream formed by the oxidization of the substituted aromatic compound; and
   recovering energy from the vapor stream in the off-gas treatment zone.

2. The process of claim 1, wherein the off-gas treatment zone comprises at least one heat exchanger, a catalytic oxidation unit, and an expander.

3. The process of claim 2, wherein the at least a portion of the vapor stream is vented upstream of the at least one heat exchanger.

4. The process of claim 2, further comprising:
   distilling the gaseous stream in a distillation column to form a distilled gaseous stream.

5. The process of claim 4, wherein the at least a portion of the vapor stream is vented to a stream leading to the catalytic oxidation unit in order to heat the distilled gaseous stream.

6. The process of claim 4, further comprising:
   directing the distilled gaseous stream to the catalytic oxidation unit, wherein the distilled gaseous stream comprises methyl bromide;
   burning hydrogen in the vapor stream in the catalytic oxidation unit;
   oxidizing methyl bromide in the catalytic oxidation unit to form bromine;
   forming a first catalytic oxidation effluent and a second catalytic oxidation effluent; and
   directing the first catalytic oxidation effluent to the expander, wherein the expander recovers energy from the first catalytic oxidation effluent.

7. The process of claim 6, further comprising:
   directing the second catalytic oxidation effluent to a scrubber; and
   removing bromine from the second catalytic oxidation effluent with the scrubber.

8. The process of claim 6, wherein the temperature of the first catalytic oxidation effluent entering the expander is greater than 150 degrees Celsius.

9. The process of claim 1, wherein the pre-heating zone comprises a heat exchanger and wherein the vapor stream enters a shell side of the heat exchanger.

10. The process of claim 1, wherein the purified aromatic carboxylic acid comprises terephthalic acid.

* * * * *